United States Patent [19]
van Groeningen

[11] Patent Number: 5,876,422
[45] Date of Patent: Mar. 2, 1999

[54] PACEMAKER SYSTEM WITH PELTIER COOLING OF A-V NODE FOR TREATING ATRIAL FIBRILLATION

[75] Inventor: Christianus J. J. E. van Groeningen, Utrecht, Netherlands

[73] Assignee: Vitatron Medical B.V., Dieren, Netherlands

[21] Appl. No.: 111,320

[22] Filed: Jul. 7, 1998

[51] Int. Cl.⁶ .................................................. A61N 1/362
[52] U.S. Cl. ..................................... 607/3; 607/14; 607/9; 606/21
[58] Field of Search ............................. 607/9, 3, 14, 96, 607/99; 606/21, 23, 22, 25, 26

[56] References Cited

U.S. PATENT DOCUMENTS

| | | | |
|---|---|---|---|
| 4,081,256 | 3/1978 | Donnelly | 62/4 |
| 4,483,341 | 11/1984 | Witteles | 128/402 |
| 4,519,389 | 5/1985 | Gudkin et al. | 128/303.1 |
| 4,780,117 | 10/1988 | Lahey et al. | 62/4 |
| 4,949,549 | 8/1990 | Steidl et al. | 62/101 |
| 4,967,573 | 11/1990 | Wilhelm | 62/530 |
| 5,048,301 | 9/1991 | Sabin et al. | 62/101 |
| 5,101,636 | 4/1992 | Lee et al. | 62/48.1 |
| 5,197,302 | 3/1993 | Sabin et al. | 62/477 |
| 5,207,674 | 5/1993 | Hamilton | 606/20 |
| 5,254,116 | 10/1993 | Baust et al. | 606/23 |
| 5,529,067 | 6/1996 | Larsen et al. | 607/101 |

OTHER PUBLICATIONS

Jorge Scaglione et al., "Reversion of Atrial Fibrillation in Dogs By Rapid Infusion of Cold Saline Solution," *NASPE Abstracts,* Apr. 1993, Part II, PACE, vol. 16.

"Implanted Device to Automatically Terminate ATrial Fibrillation by Rapid Cooling of the Right Atrium," *Research Disclosure,* Apr. 1994/207.

*Primary Examiner*—William E. Kamm
*Assistant Examiner*—Kennedy J. Schaetzle
*Attorney, Agent, or Firm*—Woodcock Washburn Kurtz Mackiewicz & Norris LLP

[57] ABSTRACT

There is provided a cardiac pacing system for dealing with dangerous atrial arrhythmias, wherein when an episode of such an arrhythmia is detected, the system operates to cool the A-V node so as to reversibly block conduction of the atrial excitations through to the ventricle, permitting uninterrupted asynchronous ventricular pacing during the episode. The system provides for an atrial lead having a Peltier element positioned toward its distal end, such that when the atrial lead distal end is affixed to the atrial heart wall, the cooling element is proximate to the A-V node. Upon detection of a dangerous atrial episode, the Peltier element is energized to cool the A-V node to point of effective block, and the pacemaker switches to asynchronous pacing. The atrial signals are continually monitored, and when the arrhythmia terminates on its own and a normal sinus rhythm is restored, the cooling is stopped, permitting the atrial excitations to be transferred through the A-V node and allowing a return of the pacemaker to a synchronous pacing mode.

16 Claims, 4 Drawing Sheets

PACEMAKER SYSTEM WITH PELTIER COOLING OF A-V NODE FOR TREATING ATRIAL FIBRILLATION

FIELD OF THE INVENTION

This invention relates to cardiac pacing systems with the capability of detecting episodes of atrial fibrillation and other atrial arrhythmias and, in particular, implantable pacing systems which response to such an episode by inhibiting conduction of atrial signals to the ventricle and pacing the ventricle asynchronously until the episode terminates naturally.

BACKGROUND OF THE INVENTION

Modern cardiac pacing systems have incorporated substantial capability for detecting and dealing with various arrhythmias. Of particular importance are atrial arrhythmias such as atrial fibrillation (AF), which is extremely dangerous to the patient. Pacemaker have attempted to deal with such arrhythmias by simply switching into an asynchronous mode, such that ventricular pacing does not try to track the dangerous atrial excitations. However, with ordinary asynchronous ventricular pacing and continued conduction of the atrial signals through the A-V node, a certain percentage of the atrial signals will get through to the ventricle and thus cause chaotic spontaneous ventricular contractions and paced contractions, resulting in an undesirable cardiac condition. Thus, patients with occasionally occurring atrial flutter or fibrillation are presently candidates for His bundle ablation, a procedure which aims to effectively alter the cardiac conduction pattern to interrupt the reentry cycles which support the high rate arrhythmia. This is, of course, a procedure which stops conduction of all atrial signals to the ventricle permanently. The result is that the ventricle needs to be paced permanently even though the atrium contracts normally most of the time. Besides the disadvantages of pacing compared to normal physiological contraction, ablation is a potentially dangerous and costly procedure, and it would be vastly preferred to have a less invasive alternative procedure.

Another technique that is in use is that of delivering a cardioversion shock to the patient's heart. This can be done during general anesthesia, which of course is impractical for a patient who has repeat and rather long-occurring episodes. Such a patient would also be a candidate for an implantable cardioverter device. However, such devices are very expensive, and the shocks are not welcome to the patient, i.e., they are painful. Further, if the episodes occur too frequently, these devices have a limited lifetime due to the energy expenditure of each shock.

Another approach known in the literature is to cool the atrium, thereby slowing conduction in the atrial tissue to the point of terminating the atrial fibrillation. See Abstract, Scaglione et al, PACE, Vol. 16, p 880, April 1993, Part II. In this approach, the entire atrium is cooled by introduction of a bolus of cold saline solution. Alternately, it has been proposed to cool the blood of the atrium by use of an electrically driven element. "Implanted Device to Automatically Terminate Atrial Filbrillation By Rapid Cooling of the Right Atrium," Research Disclosure, April 1994/207. However, to date this approach has not proven feasible for an implanted device.

Another prior art approach utilizes cooling of specific locations in the atrium in order to map the location of an arrhythmia source, followed by ablation of the tissue found to be giving rise to the arrhythmia or fibrillation. In U.S. Pat. No. 5,529,067, a catheter with a Peltier element embedded in its distal end is utilized to contact and cool the inside of the atrial wall. By moving the distal tip around and cooling different localized areas, all the time monitoring the atrial activity, the trouble spot which is the source of the arrhythmia can be found and then treated with conventional RF ablation. However, this procedure still requires the ablation therapy, which has the disadvantages set forth above.

There thus remains a substantial need for an improved system and technique for effectively inhibiting such atrial arrhythmias until the atrium can return on its own to a normal sinus rhythm, during which time the ventricle can be paced asynchronously. As used hereinafter, the term atrial fibrillation, or AF, refers broadly to the class of dangerous atrial arrhythmias, during episodes of which it is desired to inhibit conduction to the ventricles and pace asynchronously.

SUMMARY OF THE INVENTION

An implantable cardiac pacing system and technique are provided for recognizing atrial fibrillation, and responding during a such episode by blocking conduction of atrial excitation signals through the A-V node and pacing the ventricle asynchronously. Atrial signals are sensed and analyzed for high rate episodes representative of AF. A cooling element, such as a Peltier element driven by the pacemaker battery, is connected to the patient's heart proximate to the A-V node, having the capability of cooling the A-V node to a temperature sufficient to cause reversible A-V block. When an episode of AF is detected, the Peltier element is driven with a current so as to cool the node to, e.g., 4–17 degrees C., so as to block conduction therethrough. At the same time, detection of an AF episode triggers mode switching to a ventricular asynchronous mode. When the AF episode naturally ends, the drive current to the Peltier element is switched off, permitting the node to return to body temperature and resume normal conduction, so that the pacemaker only needs to pace "on demand"; that is, under normal conditions the ventricle is stimulated synchronously by the atrium or, if needed, by the pacemaker.

By positioning the Peltier element on or closely proximate to the A-V node, the node can be cooled very efficiently, enabling block with a very minimal current drain. Further, since only a small volume of cardiac tissue is cooled, the node can return to normal quickly following cessation of the AF. Effective A-V block is determined by the absence of sensed natural, or intrinsic R waves, after which the cooling is stabilized to maintain the block until atrial sensing indicates that a safe atrial sinus rhythm has returned.

DESCRIPTION OF THE PREFERRED EMBODIMENTS

Figure 1A:
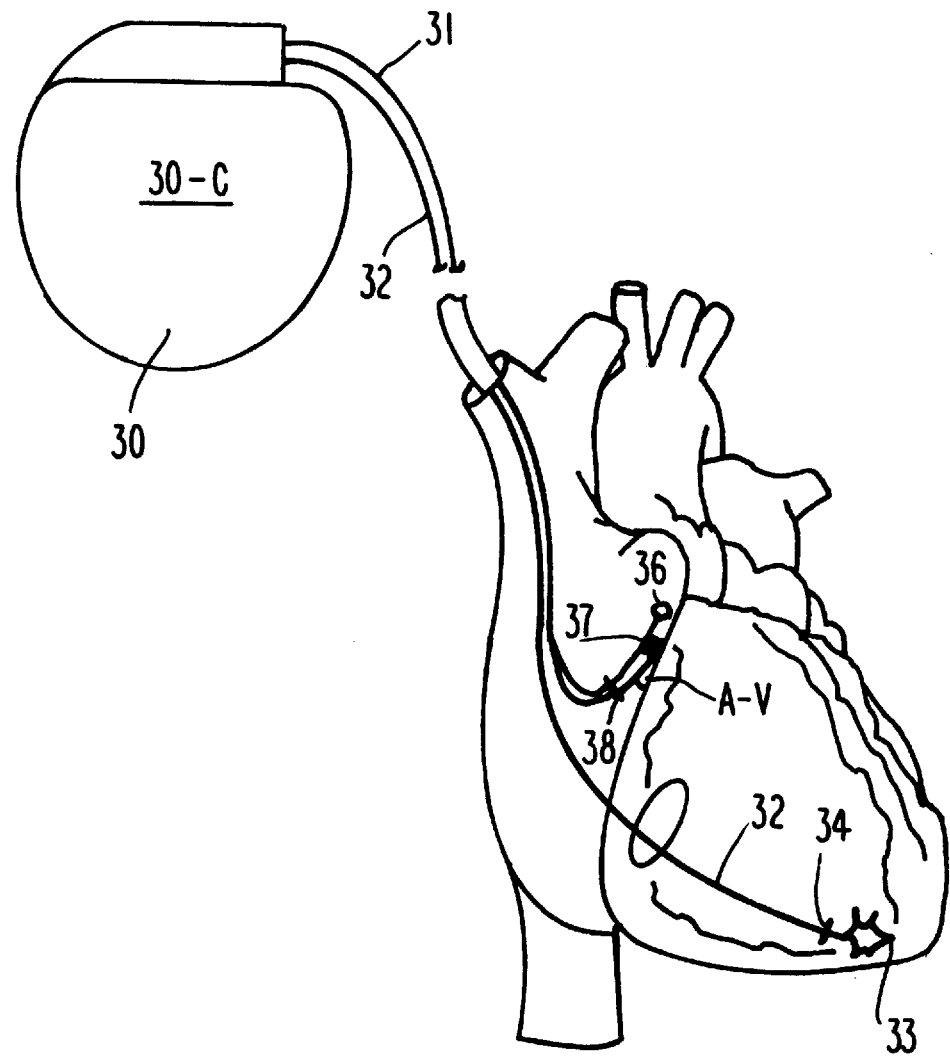
FIG. 1A is a schematic diagram of a pacemaker system in accordance with this invention, illustrating positioning of leads in the right atrium and the right ventricle, and also showing the positioning of a Peltier element on or proximate to the A-V node.

Referring first to FIG. 1A, there is shown a diagram of a pacing system in accordance with this invention. Pacemaker 30 is a dual chamber pacemaker, providing pacing pulses at least for delivery to the patient's ventricle, and preferably also providing for atrial pacing pulses. The pacemaker is encased in a pacemaker "can" 30-C, of conventional material. Ventricular pacing pulses are delivered from pacemaker 30 on lead 32, which is illustrated as being positioned with its distal end at about the apex of the right ventricle. Lead 32 may be unipolar or bipolar, and has at least one electrode, shown at 33, substantially at the distal tip, and may have a second ring electrode shown diagrammatically at 34. A second lead 31 is an atrial lead, for positioning against the inner wall of the atrium, as shown. This lead has a distal tip electrode 36, and suitably may also have a ring electrode 38 indicated as being displaced proximally from the distal end. It also carries a Peltier element 37, having a cooling surface positioned for placement in proximity to the A-V node, as indicated. The Peltier element can be positioned on or nearby the A-V node, and the term "proximate" as used herein refers to a position sufficiently close to the A-V node to enable cooling of it. It is important that the lead be fixed permanently proximate to the A-V node, which can be done best by placing it in the triangle of Koch. It is known that in this area it is difficult to attach leads passively, and accordingly in the preferred embodiment a screw-in lead is used, as illustrated in FIG. 1C. Screwing a helical tip element into the A-V node itself may or may not prove to be desirable; a safe procedure is for the physician to manipulate the separate atrial lead 31 into position so as to screw the tip end into the heart wall just proximate to the A-V node.

Figure 1B:
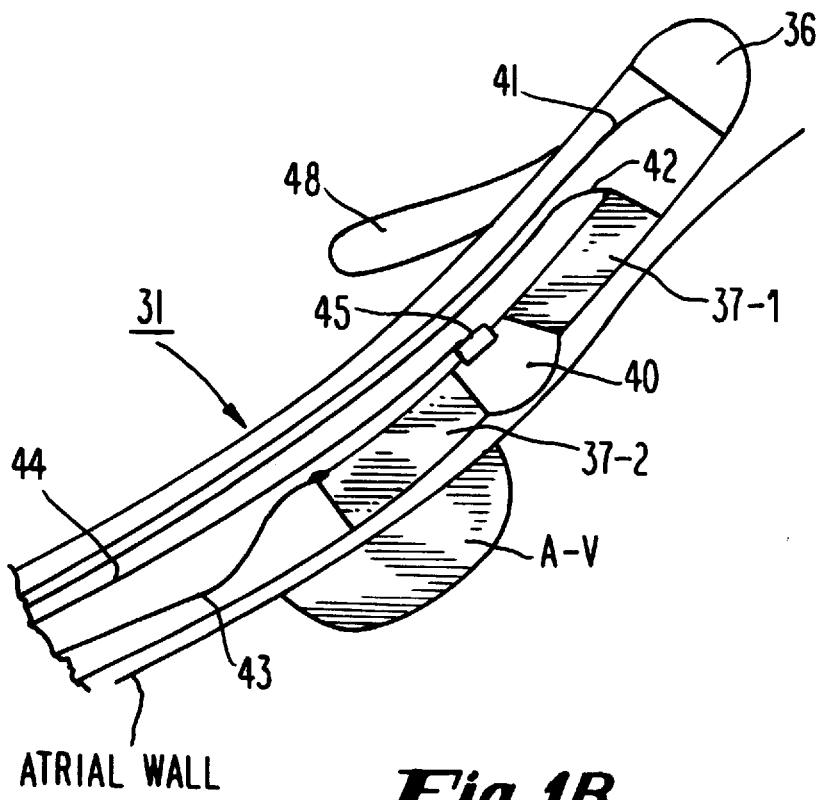
FIG. 1B is a detailed diagram of the distal end of an atrial lead in accordance with this invention.
Figure 1C:
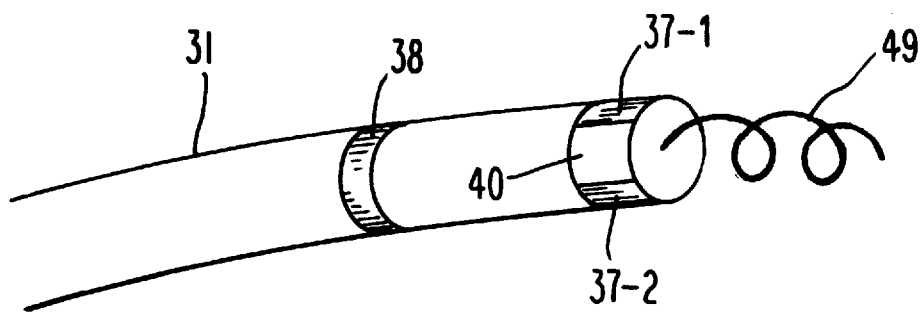
FIG. 1C is a detailed diagram of a preferred screw-in lead embodiment in accordance with this invention.
Figure 2:
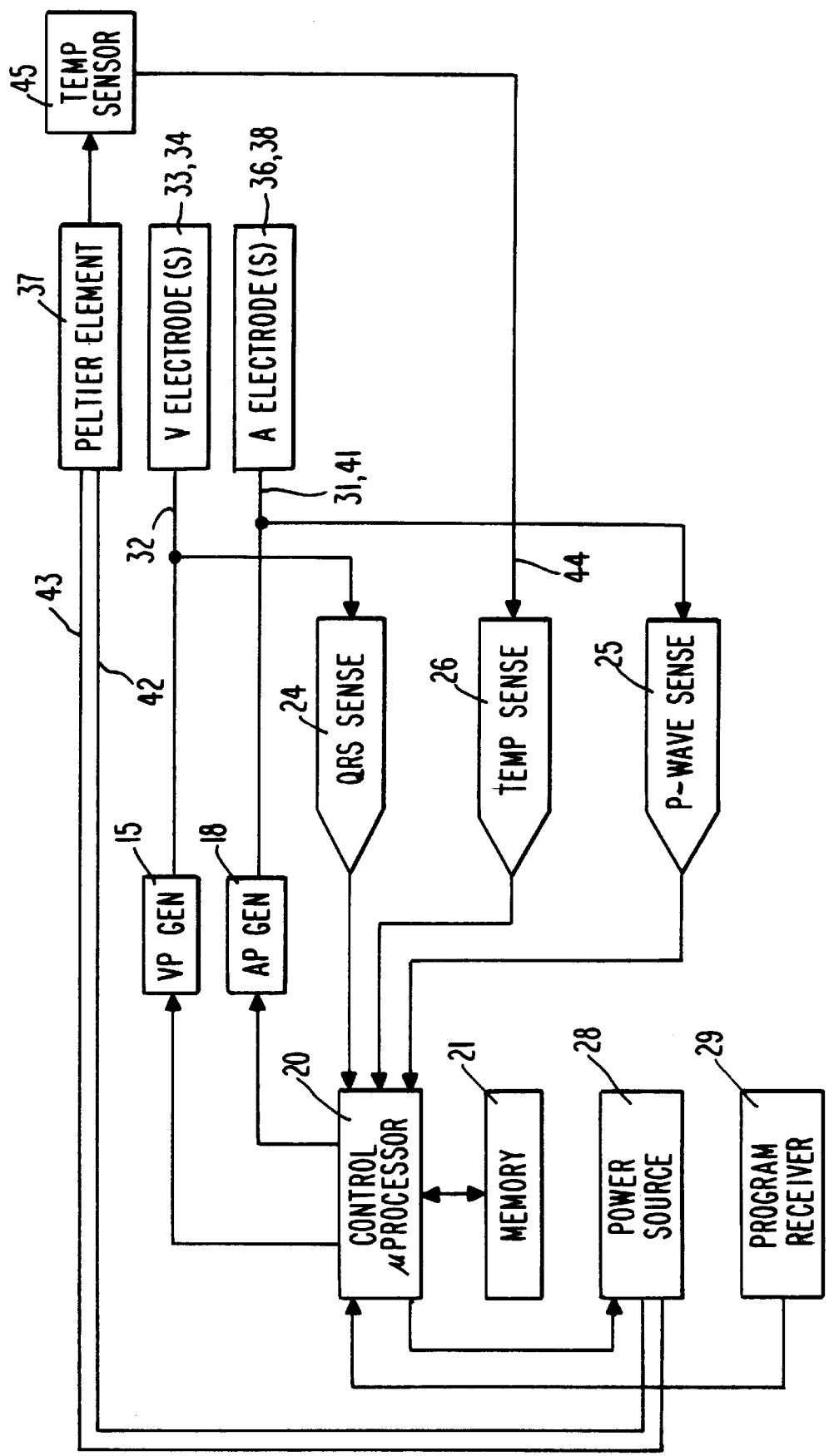
FIG. 2 is a block diagram of a pacemaker system in accordance with this invention, illustrating the control of a Peltier element which is located proximate to the patient's A-V node.

Referring now to FIG. 1B, there is shown a more detailed diagrammatic sketch of an atrial lead in accordance with this invention, carrying a Peltier element and also having one or more tines 48 to provide fixation. It is to be understood that FIG. 1B is presented to illustrate the details of the Peltier element, and that the screw-in embodiment of FIG. 1C is presently a preferred embodiment. FIG. 1B shows details of the distal end of lead 31, which otherwise has a conventional outer casing and has a proximal end (not shown) for attachment to pacemaker 30 in a known manner. The Peltier element 37 is represented by two dissimilar metals or semiconductors, 37-1 and 37-2, separated by a high heat transfer junction area 40 which is positioned proximate to the A-V node and which provides the cooling effect. The first element 37-1 of the thermocouple or Peltier element is connected to a power source, as shown in FIG. 2, by conductor 42; the second metal or semiconductor shown as 37-2 is connected to the power source by conductor 43. As is known, when current is delivered in an appropriate direction, a cooling effect is provided at the junction element 40. Also, there is a heating effect corresponding to the cooling effect, producing heat points where conductors 42 and 43 contact the respective dissimilar metallic or semiconductor elements. The Peltier element 37 is packaged to transfer the heat away from the heating points as efficiently as possible. In another embodiment, the conductors 42, 43 are made of the same respective materials as Peltier elements 37-1, 37-2, and connected to a junction area located on the pacemaker can, whereby the heat is transferred to the can surface 30-C.

In practice, the Peltier element as used in this invention can be as small as 2 mm×2 mm, and is conveniently incorporated into the lead. Also, as shown in FIG. 1B, conductor 41 connects to tip electrode 36, providing for delivery of pacing pulses from the pacemaker and delivery of sensed signals from the ventricle back to the pacemaker, in a known fashion. Further, a temperature sensing element 45 may be positioned on the cooling junction 40, and connected through conductor 44 back to the pacemaker, for monitoring the temperature of the cooling element, for control purposes as discussed further in connection with FIG. 2.

Referring to FIG. 1C, there shown diagrammatically a preferred embodiment of lead 31, having a distally positioned helical element 49, for achieving screw-in fixation to the atrial heart wall so that cooling surface 40 is positioned proximate to the A-V node. Distal element 49 may also comprise a tip electrode; a ring electrode 38 is shown for a bipolar embodiment. In this arrangement, the dissimilar Peltier materials 37-1 and 37-2 are arranged circumferentially, as opposed to the longitudinal arrangement indicated in FIG. 1B. However, the exact geometry of elements 37-1, 37-2 and 40 is a matter of design choice, the criteria being that of providing an optimum surface size for cooling element 40, as well as providing conducting heat from the heating points away from surface 40. It is anticipated that embodiments of Peltier element 37 may become available which can be incorporated into distal element 49.

Referring now to FIG. 2, there is shown a block diagram of a pacemaker system in accordance with this invention. A generator 15 is provided for generating ventricular pace pulses, under control of control block 20. The ventricular pace pulses are delivered on lead 32 to one or more ventricular electrodes 33, 34. In a preferred embodiment, the pacemaker is a VDD(R) type; however, it could be a DDD(R) type, in which case a generator 18 is provided for generating atrial pulses, which are delivered by lead 31, and in particular conductor 41, to atrial electrodes 36 and/or 38. Both generators and 18 are controlled by control block 20, which preferably incorporates a microprocessor, for control of timing, amplitude, pulse width, etc., in a known manner. Memory 21 is interconnected with control block 20, for providing software for logic control, as well as pacing parameters and other data. Programmer receiver 29 is used to receive downloaded program data from an external programmer in a known fashion, and such received data is connected through control block 20 to storage in memory 21.

Signals sensed from ventricular electrodes 33, 34 are connected through to QRS sense block 24, for appropriate signal processing and delivery to control block 20. Although not shown, the pacemaker may also sense T wave portions of the signals received from the ventricular electrodes. Likewise, signals from the atrial electrodes are connected through to P wave sense block 25, for appropriate processing and connection through to control block 20.

Of specific importance to the pacemaker system of this invention, Peltier element 37 is shown interconnected with power source 28 by conductors 42, 43. Power source 28 is controlled by control block 20 to provide current to the Peltier element in the event of an atrial arrhythmia in a manner discussed more fully in connection with FIG. 3. Also, temperature sensor 45 develops a signal representative of the temperature at cooling surface 40 of element 37, which temperature signal is connected on line 44 to the pacemaker, and to temperature sense circuitry 26, where an appropriate temperature signal is developed and connected through to control block 20. The temperature signal is utilized by control block 20 to control cooling after AV block has been achieved, e.g., limit the cooling or hold it at a steady temperature which maintains block but does not permit dangerous cooling.

Figure 3:
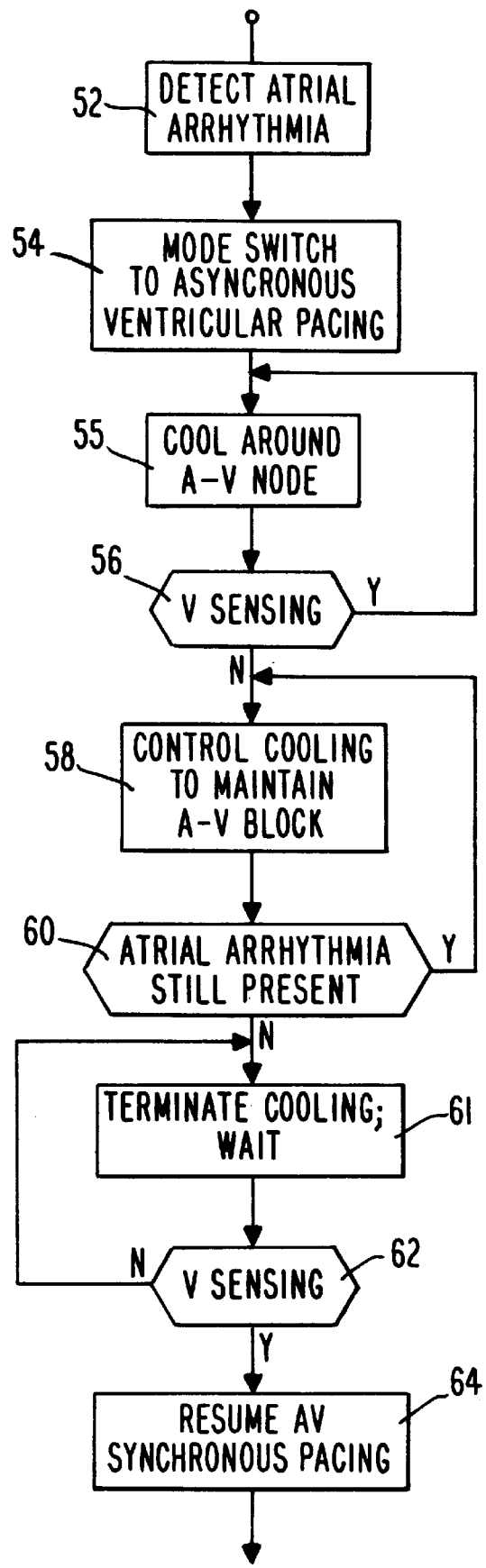
FIG. 3 is a flow diagram illustrating the primary 'steps taken by the pacing system of this invention in responding to an episode of atrial fibrillation.

Referring now to FIG. 3, there is shown a flow diagram of the steps taken in the A-V node upon detection of a dangerous atrial arrhythmia, e.g., atrial fibrillation. At block 52, the atrial arrhythmia is detected. This is done in a known manner, by monitoring the signals from the atrial electrodes, and determining when the rate has reached a dangerous level. When such a dangerous atrial arrhythmia is detected, at 54 the pacemaker mode switches to an asynchronous pacing of the ventricle. Thus, as soon as the atrial arrhythmia is detected, control block 20 controls pacing only from generator 15, and at a fixed, or asynchronous rate, such that the pacing is not affected by atrial excitations. Then, at 55, the pacemaker initiates cooling around the A-V node, controlling the power source to provide current through leads 42, 43 to Peltier element 37. At 56, the pacemaker continually monitors ventricular sensing, and determines whether ventricular excitations continue to be transmitted through the A-V node from the atrium. As long as ventricular sensing is still found, the cooling of the A-V node is continued. When and as ventricular sensing ceases, indicating A-V block due to the cooling, at 58 the pacemaker then controls cooling to maintain the block. This can be done, e.g., by limiting current to the Peltier element to maintain the temperature at or just below the sensed value when ventricular sensing ceases. Following this, the routine, shown at 60, monitors to determine whether the atrial arrhythmia is still present. This is done by continually examining the signals received from the atrial electrodes. As long as the arrhythmia is maintained, the cooling continues to maintain A-V block. When the atrial arrhythmia ceases, then at block 61 cooling is terminated allowing the A-V node to come back to normal body temperature. At 62, the pacemaker monitors ventricular sensing and when sensing reappears at 64 the control 20 resumes A-V synchronous pacing on demand, i.e., the ventricle is paced only as needed.

There is thus provided a system and method for controlled pacing of a patient's heart during episodes of atrial fibrillation and other dangerous atrial arrhythmias, which enables the patient to get through such episodes satisfactorily and obviate the need for drastic procedures, such as ablation. For a good many patients who experience such atrial episodes, the heart returns spontaneously to a normal condition, such that the episodes are basically short-term episodes that are experienced relatively infrequently. Of course, if the episodes are uncontrolled, the patient suffers. However, by providing reversible A-V block and uninterrupted asynchronous pacing through these episodes, the patient experiences very little, if anything, and as a practical matter can ride out the episodes without the need for any more invasive procedures. While the preferred embodiment of this invention utilizes a VDD or VDD(R) type pacemaker, it may also use a DDD or DDD(R) type pacemaker.

I claim:

1. A pacing system for pacing a patient's heart, having pace pulse means for generating and delivering pacing pulses to at least the patient's ventricle, sensing means for sensing atrial and ventricular natural beats, and mode means for controlling the mode of pacing, said mode control means normally controlling said pacemaker to pace the patient's ventricle synchronously with respect to sensed atrial intrinsic beats in the absence of sensed intrinsic ventricular beats, comprising:

arrhythmia means for detecting from sensed atrial beats when the patient has an episode of a dangerous atrial arrhythmia;

cooling means for lowering the temperature of the patient's A-V node so as produce a state of reversible A-V block; and temperature control means for enabling said cooling means to cool said A-V node whenever a said episode is detected, thereby blocking condition through the patient's A-V node; and said mode means comprising switching means for switching said pacemaker to an asynchronous ventricular pacing mode whenever a said episode is detected.

2. The pacing system as described in claim 1, wherein said arrhythmia means comprises episode end means for determining the end of a said episode, and said mode means comprises means for switching said pacemaker to a synchronous ventricular pacing mode when a said episode end is determined.

3. The pacing system as described in claim 2, wherein said temperature control means comprises means for disabling said cooling means whenever a said end is detected.

4. The pacing system as described in claim 3, wherein said temperature control means comprises limit means for limiting the cooling of said A-V node to a predetermined temperature.

5. The pacing system as described in claim 1, wherein said cooling means comprises a Peltier element and means for positioning said Peltier element proximate to the patient's A-V node.

6. The pacing system as described in claim 5, wherein said cooling means comprises current drive means for driving said Peltier element with current so as to produce cooling or heating.

7. The pacing system as described in claim 1, comprising an atrial lead carrying a Peltier element, said lead having a screw-in fixation element at its distal end.

8. A method of sensing and responding to atrial arrhythmias, comprising:

detecting an episode of an atrial arrhythmia in a patient;

initiating cooling proximate to the patient's A-V node, and cooling said node sufficiently to reversibly block conduction therethrough;

pacing the patient's ventricle asynchronously during said episode;

continually monitoring atrial signals while said node is blocked, and determining when said episode has terminated; and in response to a determined termination of a said episode, stopping cooling of said A-V node, and pacing said patient on demand.

9. The method as described in claim 8, comprising monitoring ventricular excitations after initiating cooling of the A-V node, determining when conduction of signals through said A-V node has stopped and block has been achieved, and controlling said cooling sufficient to maintain A-V block as long as said episode continues.

10. A pacing system for pacing a patient, having pace pulse means for generating and delivering pacing pulses to at least the patient's ventricle, sensing means for sensing atrial and ventricular natural beats, and mode control means for controlling the mode of pacing the patient's ventricle, comprising:

means for detecting from sensed atrial beats when the patient has a dangerous atrial arrhythmia;

said mode control means having means for controlling said pacemaker to operate in an asynchronous ventricular pacing mode when said dangerous atrial arrhythmia is detected; and block means for reversibly blocking conduction through the patient's A-V node during a said dangerous atrial arrhythmia.

11. The system as described in claim 10, wherein said block means comprises cooling means for cooling the patient's A-V node to a point of reversible A-V block.

12. The system as described in claim 11, wherein said cooling means comprises a Peltier element and drive means for driving said Peltier element to control its cooling operation.

13. The system as described in claim 10, wherein said mode control means has synchronous means for normally controlling said pacemaker to pace the patient's ventricle synchronously with respect to sensed atrial natural beats in the absence of natural ventricular beats, and switching means for switching operation to said asynchronous mode whenever a said dangerous atrial arrhythmia is present.

14. The system as described in claim 10, wherein said block means comprises cooling means for cooling the patient's heart in the vicinity of the AV node, thereby reversibly blocking conduction through said AV node for the duration of said cooling.

15. The system as described in claim 14, providing heat transfer means for transferring heat generated as a by-product of said cooling away from the vicinity of the AV node.

16. The system as described in claim 15, comprising a pacemaker encased in a can, and wherein said heat transfer means comprises means for transferring said heat to said pacemaker can.

* * * * *